United States Patent
De Beni et al.

(10) Patent No.: US 10,130,328 B2
(45) Date of Patent: Nov. 20, 2018

(54) METHOD AND APPARATUS FOR ULTRASOUND IMAGE ACQUISITION

(71) Applicants: ESAOTE SPA, Genoa (IT); MEDCOM GMBH, Darmstadt (DE)

(72) Inventors: Stefano De Beni, Genoa (IT); Leonardo Forzoni, Pistoia (IT); Sara D'Onofrio, Novara (IT); Velizar Kolev, Darmstadt (DE); Georgios Sakas, Darmstadt (DE)

( * ) Notice: Subject to any disclaimer, the term of this patent is extended or adjusted under 35 U.S.C. 154(b) by 648 days.

(21) Appl. No.: 14/423,424

(22) PCT Filed: Sep. 4, 2013

(86) PCT No.: PCT/IB2013/058283
§ 371 (c)(1),
(2) Date: Feb. 23, 2015

(87) PCT Pub. No.: WO2014/060868
PCT Pub. Date: Apr. 24, 2014

(65) Prior Publication Data
US 2015/0209002 A1 Jul. 30, 2015

(30) Foreign Application Priority Data
Sep. 10, 2012 (EP) .................................. 12183753

(51) Int. Cl.
*A61B 8/08* (2006.01)
*A61B 8/00* (2006.01)
(Continued)

(52) U.S. Cl.
CPC ............ *A61B 8/0808* (2013.01); *A61B 5/055* (2013.01); *A61B 8/06* (2013.01); *A61B 8/4245* (2013.01);
(Continued)

(58) Field of Classification Search
None
See application file for complete search history.

(56) References Cited

U.S. PATENT DOCUMENTS

| 2001/0031919 A1 | 10/2001 | Strommer et al. |
| 2005/0033173 A1 * | 2/2005 | Von Behren ............. A61B 8/00 600/443 |

(Continued)

OTHER PUBLICATIONS

Gobbi D G et al, Ultrasound/MRI overlay with image warping for neurosurgery, Lecture Notes in Computer Science, vol. 1935, Oct. 14, 2000, pp. 106-114 Sections 2 and 3.

*Primary Examiner* — Katherine Fernandez
(74) *Attorney, Agent, or Firm* — Themis Law

(57) ABSTRACT

Method for ultrasound image acquisition includes defining a fixed frame of reference, with an origin of coordinates within a transmitter of a tracking system; detecting position and orientation of a probe relative to the frame of reference with a probe sensor of the tracking system coupled to the probe; detecting position and orientation of a body relative to the frame of reference with a reference sensor of the tracking system coupled to the body; calculating position and orientation of the probe with respect to the body; acquiring a set of 2D images constituting a 3D by transmitting an ultrasonic beam into the body and receiving echographic signals with the probe; iterating for a predetermined number of 3D image acquisitions; generating a panoramic 3D image by combining the 2D images based on information of position and orientation of the probe relative to the body for each 2D image acquisition.

5 Claims, 3 Drawing Sheets

Figure 1:
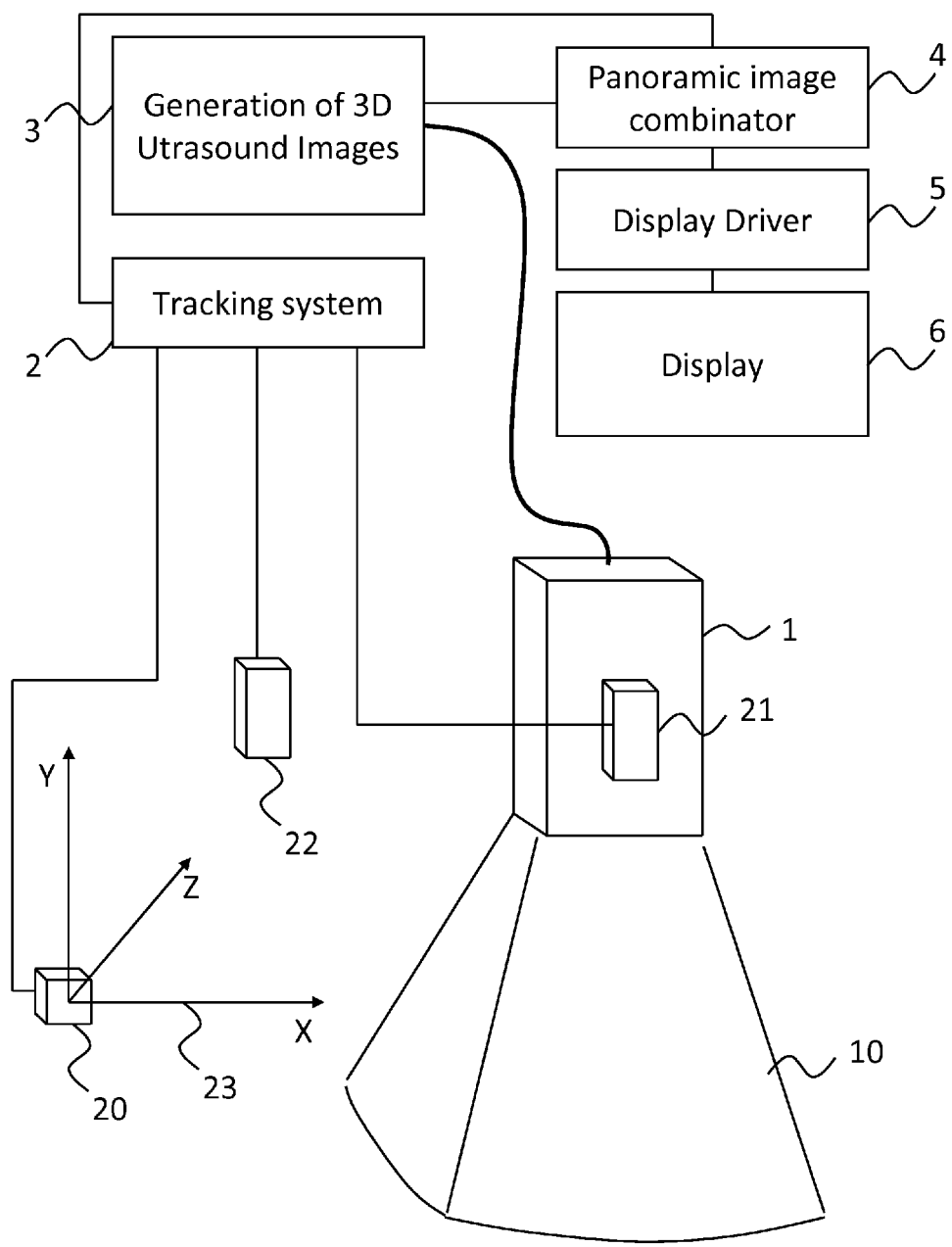

(51) Int. Cl.
  *G01S 15/89* (2006.01)
  *G01S 7/52* (2006.01)
  *A61B 5/055* (2006.01)
  *A61B 8/06* (2006.01)
  *G06T 7/00* (2017.01)

(52) U.S. Cl.
  CPC ............ *A61B 8/4254* (2013.01); *A61B 8/483* (2013.01); *A61B 8/5261* (2013.01); *G01S 7/52065* (2013.01); *G01S 15/899* (2013.01); *G01S 15/8925* (2013.01); *G01S 15/8936* (2013.01); *G01S 15/8988* (2013.01); *G01S 15/8993* (2013.01); *G06T 7/0012* (2013.01); *G06T 2207/10136* (2013.01)

(56) References Cited

U.S. PATENT DOCUMENTS

| | | | |
|---|---|---|---|
| 2007/0255137 A1 | 11/2007 | Sui et al. | |
| 2008/0269604 A1* | 10/2008 | Boctor | A61B 8/00 600/437 |
| 2009/0018445 A1* | 1/2009 | Schers | A61B 8/0875 600/437 |
| 2011/0257514 A1* | 10/2011 | Bucki | G06T 7/0038 600/420 |

\* cited by examiner

METHOD AND APPARATUS FOR ULTRASOUND IMAGE ACQUISITION

The present invention relates to a method for ultrasound image acquisition, comprising the following steps:

a) defining a fixed frame of reference, the origin of coordinates being set within a transmitter of a tracking system;

b) detecting position and orientation of a probe with respect to said frame of reference by means of a probe sensor of said tracking system coupled to said probe;

c) detecting position and orientation of a body to be imaged with respect to said frame of reference by means of a reference sensor of said tracking system coupled to said body;

d) calculating position and orientation of said probe with respect to said body;

e) acquiring a set of 2D images constituting a 3D image in Doppler mode by transmitting an ultrasonic beam into said body and receiving ecographic signals from said body by said probe;

f) iterating points b) to e) for a predetermined number of 3D image acquisitions;

g) generating a panoramic 3D image combining the 2D images of the acquired 3D images on the basis of the information of position and orientation of said probe with respect to said body calculated for each 2D image acquisition.

The present invention is intended in a medical diagnostic framework, and the body to be imaged comprises the anatomical structures of a patient, but can also be applied in other similar technical fields.

Currently used methods for ultrasound image acquisition generating a panoramic 3D image combining multiple acquired 3D images must take into account the relative position and orientation of the probe and the body to be imaged.

The position and orientation of the probe is usually tracked with a tracking system comprising a fixed transmitter defining a frame of reference and a probe sensor coupled to the probe.

The information of position and orientation of the probe is associated to each image acquisition, so that it can be used to correctly combine the images in a panoramic image.

The panoramic 3D image allows a wider field of view than each single image and is thus used in imaging anatomical structures with larger dimensions.

The known methods work well when the body to be imaged does not move, i.e. there is no displacement of the body relative to the fixed frame of reference, hence the fixed frame of reference defined by the transmitter is the frame of reference of the body.

That means that the position and orientation of the probe relative to the fixed frame are also relative to the body.

In many occasions, however, the body to be imaged can't be maintained motionless and the reconstruction of the panoramic image can be severely compromised in case of little movements or eventually made impossible in case of large movements.

In fact if the patient is moved, the coordinates of the acquired images with respect to the transmitter change and the 3D panoramic combination is not possible.

This applies for example in case of pathological conditions of the patient, in particular when the patient is affected by a neural disease and can't stay motionless for the whole time required for ultrasound examination.

Another critical situation is represented by specific examinations that need the movement of the body for imaging reasons, for example the transcranial imaging, in which the head of the patient has to be moved in different positions during the image acquisition in order to obtain good images.

In the case of transcranial acquisitions, there are anatomically only few transcranial acquisition windows feasible for imaging, therefore the probe must be often considerably displaced from one side of the head to another to be positioned by the few available acquisition windows, with the risk of movements of the patient.

It is impossible from a practical point of view to move the head of the examined subject to perform a first acquisition and then to reposition the head in the same exact position in order to acquire a contralateral volume.

Usually in these cases the head of the patient is immobilized to avoid movements, and this worsen the comfort of the patient.

The aim of the present invention is to overcome the problems of the known methods, providing a method for ultrasound image acquisition which, by means of relatively simple and inexpensive arrangements, allows to refer the position and orientation of the probe to the body and is thus immune to errors due to motion.

Whatever be the movements of the patient, all the acquired 2D images can be combined without problems in a panoramic image since every 2D image is associated to the information relating the position and orientation of the probe relative to the body and not to the transmitter.

In case of pathological conditions, this avoids the need of immobilizing the patient with constrains to hold him/her still.

The method is aimed to vascular investigation and the Doppler mode can comprise color Doppler or power Doppler. In one example the user can select what to see, for instance erasing completely the B-Mode information so that only the Doppler information relative to the vessels is maintained.

The method allows to correct each 2D image position during the 3D scan, so if the patient moves during the scan it is possible to compensate such movement.

In a preferred embodiment, step d) comprises the following steps:

h) generating from the detected position and orientation of the probe a rotation matrix RP indicating the rotation and translation transforming the fixed frame of reference into the frame of reference of the probe;

i) generating from the detected position and orientation of the body a rotation matrix RR indicating the rotation and translation transforming the fixed frame of reference into the frame of reference of the body;

j) multiplying the rotation matrix RP with the inverse of the rotation matrix RR in order to obtain a calculated rotation matrix RP' indicating the rotation and translation transforming the frame of reference of the body into the frame of reference of the probe.

The calculation can be performed automatically by a computer program.

The use of rotation matrices allows a powerful mathematical tool to represent rotation and translation of the different frames of reference positioned respectively of the transmitter, of the probe and of the patient and can thus indicate the position and orientation of the patient with respect to the transmitter and the position and orientation of the probe with respect to the transmitter and eventually to the patient.

According to a further embodiment, the said body is the head of a patient, said acquisitions being transcranial acquisitions.

Preferably the reference sensor is coupled to the forehead of the patient.

This application is particularly advantageous because the problems listed above relating the transcranial acquisitions are solved by referring the information of position and orientation of the probe to the body.

During the acquisitions, the head can be rotated in the positions needed or convenient for the operator, without losing correspondence between the image scanned and the detected position and orientation of the probe.

In transcranial sonography, since the interest is focused on the vessels and the brain structures, the bone structures represent a physical limit for the brain insonation.

The method is particularly advantageous for stroke detection and similar intracranial vascular problems.

In an embodiment the acquisition is performed by means of a 2D probe.

Preferably the acquisition by means of the 2D probe is performed manually.

This allows for an easy scan through the temporal bone window, which is used by transcranial Doppler sonography, and which is difficult to scan with 3D motorized or matrix probes, due to its reduced size.

A manual acquisition with a 2D probe also allows for a slow acquisition, which is necessary in order to properly reconstruct the vessels without artifacts in Doppler mode, which artefacts can be due to fast probe movements.

In fact, particularly in power Doppler scans, the probe cannot move fast due to limited ultrasound Doppler mode frame rate and the possibility of generation of artifacts due to probe movements.

It is important to have high quality since the vessels to be imaged are very thin.

In a further embodiment, said panoramic 3D image is automatically fused with a corresponding volumetric image of the same patient acquired in a different imaging modality.

Different imaging modalities can be preferably MRI, but also CT, PET, SPECT or similar, or a combination or fusion thereof.

According to an improvement, the images are fused by means of an automatic registration algorithm performing a matching of the vessels comprised in the panoramic 3D image with the vessels identified by segmentation in the volumetric image acquired in said different imaging modality.

In an exemplary embodiment a previously acquired MRI volumetric image is automatically registered to the panoramic 3D image of the color Doppler or power Doppler signals of the cerebral vessels of the examined patient.

The auto-registration is launched by the operator, which manually roughly detects within the panoramic 3D image an anatomical marker, like for example the circle of Willis and the other main arteries.

The anatomical marker can also be detected in a single 3D image, before the generation of the panoramic image.

The operator also detects within the volumetric MRI image an axial plane containing at least partially the above mentioned vessels.

After this rough manual detection the automatic registration algorithm starts to automatically match the panoramic 3D image, which is a reconstruction of Doppler signals, with the related vessels present within the volumetric MRI image.

The MRI image or other imaging modality image can be advantageously acquired with contrast medium to enhance the contrast of the vessels.

This improvement allows to register and fuse the ultrasound panoramic 3D image with a volumetric image acquired with a different imaging modality, which can have a higher spatial resolution, which is the case of MRI images.

Also the co-registration of the panoramic 3D image with the volumetric image acquired in a different imaging modality benefits of the information of position and orientation of the probe with respect to the body calculated for each 2D image acquisition, so that the voluntary or involuntary movements of the patient are enabled and are not a problem for the acquisition. In a variant embodiment, rather than a volume to volume registration between ultrasound and magnetic resonance 3D images, it is possible to acquire a single 2D ultrasound image and to register it with the magnetic resonance image volume.

Further acquired ultrasound 2D images can then be combined with the first 2D image to form the 3D images, and they are automatically registered to the MRI volume, or they can be treated as single images registered to the MRI volume.

The present invention relates also to an apparatus for ultrasound image acquisition, comprising a probe having at least one piezoelectric transducer, a stage for transmitting an ultrasonic beam by said at least one transducer into a body to be imaged, a stage for receiving and processing echographic signals returned to the at least one transducer.

Also in this case, the known apparatuses suffer of the above mentioned problems since the position and orientation of the probe can only be referred to the fixed frame of reference defined by the transmitter, and the reconstruction of panoramic images is hence prone to distortions or failures caused by motion of the patient.

These problems are solved providing a tracking system which comprises a transmitter defining a fixed frame of reference and a probe sensor coupled to the probe, said probe sensor detecting the position and orientation of the probe with respect to said fixed frame of reference, so that multiple acquisitions in Doppler mode of 2D images constituting 3D images are performed, and they are combined in a panoramic 3D image using said information of position and orientation of the probe for each 2D image acquisition, a reference sensor being provided coupled to the body to be imaged, said reference sensor detecting the position and orientation of the body with respect to said fixed frame of reference, said tracking system comprising means for calculating the position and orientation of the probe with respect to the body.

According to a preferred embodiment, said transmitter, said probe sensor and said reference sensor are of electromagnetic type.

According to a further embodiment said probe is a 2D probe.

Other type of tracking system can be provided, for example optical or acoustic.

Figure 2:
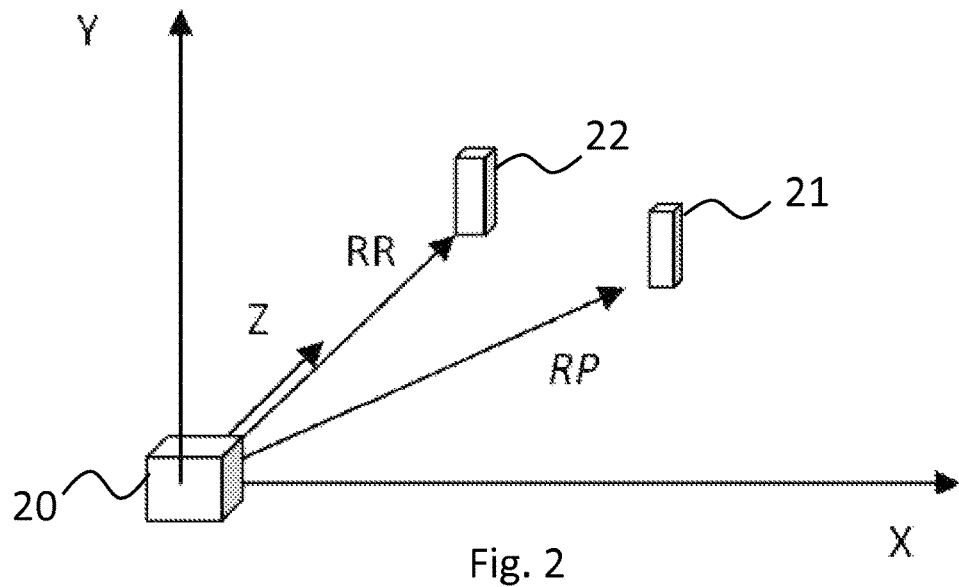
Figure 3:
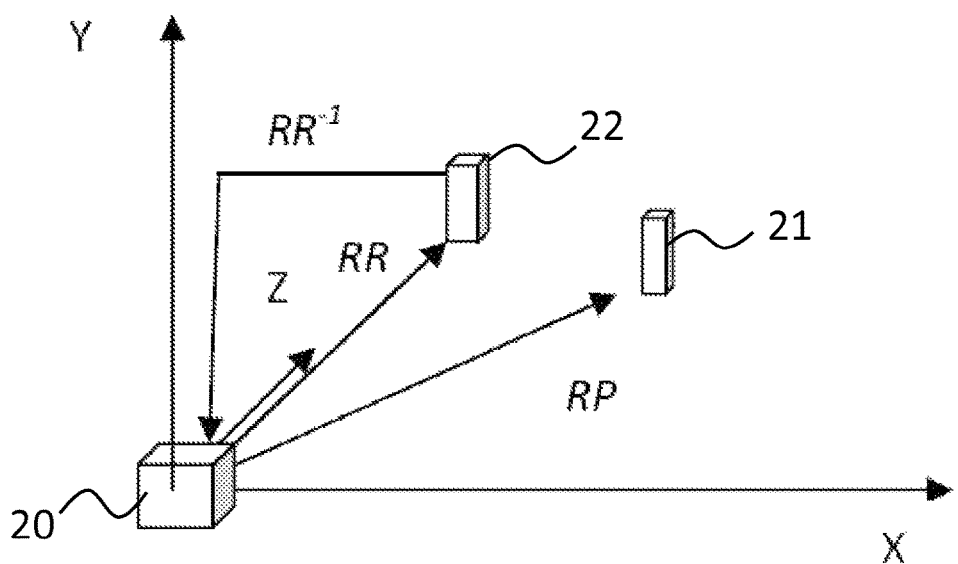
Figure 4:
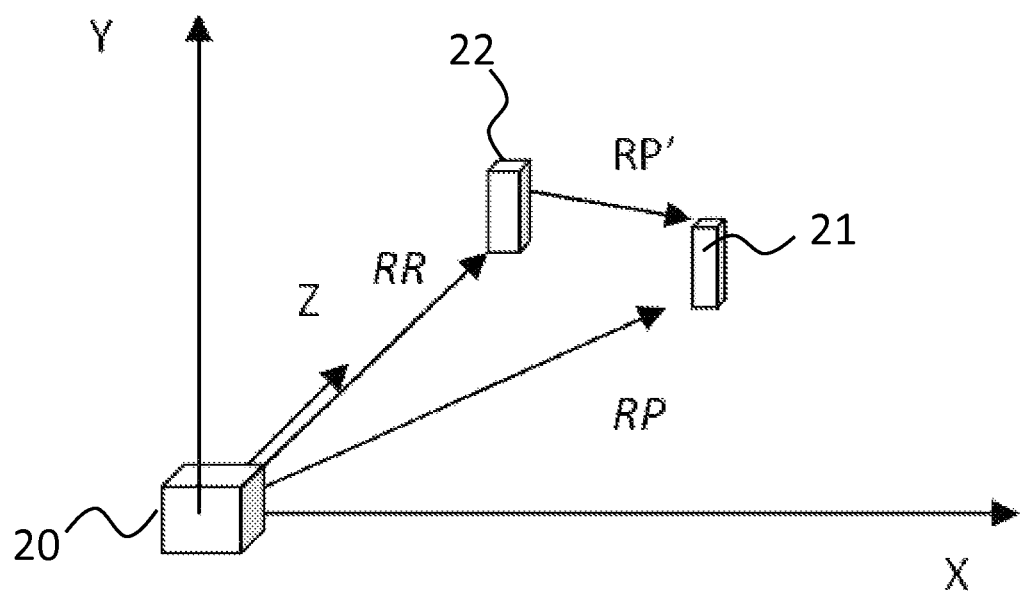

These and other features and advantages of the present invention will appear more clearly from the following description of some embodiments, illustrated in the annexed drawings, wherein:

FIG. 1 shows an embodiment of the apparatus according to the present invention;

FIGS. 2 to 4 explain the coordinates transformations provided in the method according to the present invention.

In FIG. 1 an apparatus for ultrasound image acquisition is shown, which apparatus comprises an ultrasound probe 1 having at least one piezoelectric transducer, a stage for transmitting an ultrasonic beam by said at least one transducer into a body to be imaged, a stage for receiving and processing echographic signals returned to the at least one transducer.

The probe 1 is of 2D type and acquires subsequent 2D images in order to generate 3D images from a scan volume 10, said stage for receiving and processing echographic signals being comprised in a unit for generation of 3D ultrasound images 3.

The tracking system 2 comprises a transmitter 20 defining a fixed frame of reference 23 and a probe sensor 21 coupled to the probe 1 in a fixed way so that a rotation and/or translation of the probe 1 corresponds to a rotation and/or translation of the probe sensor 21.

The probe sensor 21 detects its position and orientation with respect to said fixed frame of reference 23 and consequently detects the position of the probe 1 with respect to said fixed frame of reference 23.

The probe sensor 21 is preferably mounted to the probe shaft.

A reference sensor 22 is coupled to the body to be imaged in a fixed way so that a rotation and/or translation of the body corresponds to a rotation and/or translation of the reference sensor 22.

The reference sensor 22 detects its position and orientation with respect to said fixed frame of reference 23 and consequently detects the position of the body with respect to said fixed frame of reference 23.

The reference sensor 22 is preferably mounted to the head of the patient, in particular to the forehead, for example by means of an elastic strap or of a strap provided with closing means such as Velcro® endings.

Preferably the transmitter 20, the probe sensor 21 and the reference sensor 22 are of electromagnetic type, i.e. they function by measuring the strength of the magnetic fields generated by the electric current which flows through three small wire coils, oriented perpendicular to one another.

The current causes each wire to work as an electromagnet while the current is flowing through it.

By sequentially activating each of the wire coils of the transmitter 20, and measuring the magnetic fields generated on each of the three perpendicular wire coils of the probe sensor 21 and of the reference sensor 22, it is possible to determine the position and orientation of the probe sensor 21 and of the reference sensor 22 with respect to the transmitter 20.

The tracking system 2 comprises means calculating the position and orientation of the probe sensor 21 with respect to the reference sensor 22, hence calculating the position and orientation of the probe 1 with respect to the body.

Multiple acquisitions of 3D images are then performed, each 3D image being composed by a plurality of 2D images, and for each 2D image the position and orientation of the probe 1 with respect to the body is calculated.

The acquired images are combined in a panoramic image by a panoramic image combinator 4, using said information of position and orientation of the probe for each 2D image acquisition to correct the position of each 2D image.

The panoramic image obtained is visualized onto a display 6 by means of a display driver 5.

The method steps carried out by the tracking system 2 are shown in FIGS. 2 to 4.

The coordinates of the probe sensor 21 have to be converted from being based on the position of the transmitter 20 to being based on the position of the reference sensor 22 placed on the patients head.

The reference sensor 22 also has coordinates in transmitter coordinate system, and these coordinates change continuously with any patient movement because the sensor is fixed to the head.

As shown in FIG. 2, the coordinates of the probe sensor 21 with respect to the transmitter 20 are read and a rotation matrix RP is generated.

The rotation matrix RP contains both the rotation and translation of the probe sensor 21 in the frame of reference 23 with origin in the transmitter 20.

Also the coordinates of the reference sensor 22 with respect to the transmitter 20 are read and a rotation matrix RR is generated.

The rotation matrix RR contains both the rotation and translation of the reference sensor 22 in the frame of reference 23 with origin in the transmitter 20.

As shown in FIG. 3, the coordinates of the reference sensor 22 represented by matrix RR are inverted and saved in matrix $RR^{-1}$.

Multiplying the coordinates of the reference sensor 22 with its inversion puts the reference sensor back to the origin of the frame of reference 23 where the transmitter 20 is, i.e. $RR \cdot RR^{-1} = 1$.

As shown in FIG. 4, the coordinates of the probe sensor 21 are multiplied with the inverted coordinates of the reference sensor 22.

This puts the probe sensor 21 to a position relative to the reference sensor 22, creating a rotation matrix RP' of the probe sensor 21 with respect to the reference sensor 22, i.e. $RP \cdot RR^{-1} = RP'$, and can thus identify the position and orientation of the probe 1 with respect to the body.

For example, if both sensors experience the same translation and rotation, as they were fixed to each other, during the motion the calculation means will yield the same coordinates for the probe sensor 21, no matter where it is positioned with respect to the transmitter 20.

This happens due to the fact that the reference sensor 22 coordinates are translated to the origin and orientated in such a way that their axes match the transmitter 20 coordinate system axes.

The invention claimed is:

1. A method for ultrasound image acquisition, comprising:
   a) defining a fixed frame of reference, an origin of coordinates being set within a transmitter of a tracking system;
   b) detecting position and orientation of a probe with respect to said fixed frame of reference with a probe sensor of said tracking system coupled to said probe;
   c) detecting position and orientation of a body to be imaged with respect to said frame of reference with a reference sensor of said tracking system coupled to said body;
   d) calculating the position and the orientation of said probe with respect to said body;
   e) acquiring a set of 2D images constituting a 3D image in Doppler mode by transmitting an ultrasonic beam into said body and receiving ecographic signals from said body by said probe;
   f) iterating steps b) to e) for a predetermined number of 3D image acquisitions; and
   g) generating a panoramic 3D image combining the 2D images of the acquired 3D images based on information of the position and the orientation of said probe with respect to said body calculated for each 2D image acquisition,
   wherein step d) comprises the following steps:
   h) generating from the detected position and orientation of the probe a rotation matrix RP indicating rotation and translation transforming the fixed frame of reference into a frame of reference of the probe;

i) generating from the detected position and orientation of the body a rotation matrix RR indicating rotation and translation transforming the fixed frame of reference into a frame of reference of the body; and j) multiplying the rotation matrix RP with the inverse of the rotation matrix RR in order to obtain a calculated rotation matrix RP' indicating rotation and translation transforming the frame of reference of the body into the frame of reference of the probe.

2. The method as claimed in claim 1, wherein the body is a head of a patient, said acquisitions being transcranial acquisitions.

3. The method as claimed in claim 1, wherein the step of acquiring a set of 2D images is performed with a 2D probe.

4. The method as claimed in claim 1, wherein said panoramic 3D image is automatically fused with a corresponding volumetric image of a same patient acquired in a different imaging modality.

5. The method as claimed in claim 4, wherein the images are fused using an automatic registration algorithm performing a matching of vessels comprised in the panoramic 3D image with vessels identified by segmentation in the volumetric image acquired in said different imaging modality.

* * * * *